United States Patent
Augustin et al.

(10) Patent No.: US 11,627,974 B2
(45) Date of Patent: Apr. 18, 2023

(54) IMPLANT FOR MEDICAL USE INTENDED TO CLIP TO A BIOLOGICAL PROTUBERANCE

(71) Applicant: DIANOSIC, Malakoff (FR)

(72) Inventors: Marc Augustin, Paris (FR); Philippe Bastide, Issy-les-Moulineaux (FR)

(73) Assignee: DIANOSIC, Strasbourg (FR)

( * ) Notice: Subject to any disclaimer, the term of this patent is extended or adjusted under 35 U.S.C. 154(b) by 583 days.

(21) Appl. No.: 16/635,946

(22) PCT Filed: Jul. 19, 2018

(86) PCT No.: PCT/FR2018/051848
§ 371 (c)(1),
(2) Date: Jan. 31, 2020

(87) PCT Pub. No.: WO2019/025695
PCT Pub. Date: Feb. 7, 2019

(65) Prior Publication Data
US 2021/0145467 A1    May 20, 2021

(30) Foreign Application Priority Data
Aug. 3, 2017   (FR) ...................... 1757468

(51) Int. Cl.
*A61B 17/24*    (2006.01)
*A61B 90/00*    (2016.01)
*A61B 17/00*    (2006.01)

(52) U.S. Cl.
CPC .............. *A61B 17/24* (2013.01); *A61B 90/04* (2016.02); *A61B 90/08* (2016.02);
(Continued)

(58) Field of Classification Search
CPC ........ A61F 5/08; A61F 2/186; A61F 13/2005; A61B 17/24; A61B 2090/0816; A61B 2017/00889; A61B 2017/00893
See application file for complete search history.

(56) References Cited

U.S. PATENT DOCUMENTS 3,188,605 A * 6/1965 Slenker .................. H01R 11/22
                                                                439/829
5,094,233 A    3/1992 Brennan
(Continued)

FOREIGN PATENT DOCUMENTS

CN    1729029 A    2/2006
CN    1953778 A    4/2007
(Continued)

OTHER PUBLICATIONS

International Search Report, dated Dec. 3, 2018, from corresponding PCT application No. PCT/FR2018/051848, 5 pages.
(Continued)

*Primary Examiner* — Katherine M Shi
*Assistant Examiner* — Nash A Baset
(74) *Attorney, Agent, or Firm* — Nixon & Vanderhye

(57) ABSTRACT

Disclosed is an implant intended to be introduced into a human or animal body cavity, and includes two walls intended to grip between them a biological protuberance present in the cavity in order to attach the implant to the biological protuberance. Each wall includes a structural element having corrugations such that the structural element is folded up on itself several times, enabling the wall to be folded up before the introduction of the implant, then deployed inside the cavity.

20 Claims, 5 Drawing Sheets

(52) U.S. Cl.
CPC ............. *A61B 2017/00004* (2013.01); *A61B 2017/00867* (2013.01); *A61B 2017/00889* (2013.01); *A61B 2017/00893* (2013.01); *A61B 2090/0816* (2016.02)

(56) References Cited

U.S. PATENT DOCUMENTS

| | | | |
|---|---|---|---|
| 6,565,581 B1* | 5/2003 | Spence | ............. A61B 17/1152 606/153 |
| 2003/0153932 A1 | 8/2003 | Spence et al. | |
| 2004/0002721 A1* | 1/2004 | Podmore | ............. A61B 17/115 606/155 |
| 2008/0281300 A1 | 11/2008 | Morriss | |
| 2013/0276794 A1 | 10/2013 | Morriss | |
| 2013/0338700 A1 | 12/2013 | Matheny | |
| 2016/0095599 A1* | 4/2016 | Jose | ............. A61B 17/11 606/154 |
| 2016/0374800 A1 | 12/2016 | You et al. | |
| 2021/0030927 A1 | 2/2021 | Eaton et al. | |

FOREIGN PATENT DOCUMENTS

| | | |
|---|---|---|
| CN | 101945621 A | 1/2011 |
| CN | 103384507 A | 11/2013 |
| DE | 20314392 U1 | 4/2004 |
| JP | 2015-181784 A | 10/2015 |

OTHER PUBLICATIONS

Office Action issued in Chinese Patent Application No. 201880061566.1 dated Oct. 26, 2022, 15 Pages.

* cited by examiner

IMPLANT FOR MEDICAL USE INTENDED TO CLIP TO A BIOLOGICAL PROTUBERANCE

BACKGROUND OF THE INVENTION

Field of the Invention

The present invention relates to an implant for medical use intended to clip to a biological protuberance.

The invention applies more particularly to an implant for medical use intended to be introduced into a cavity of a human or animal body, including at least one clip comprising two walls intended to grip therebetween a biological protuberance present in the cavity in order to attach the implant to the biological protuberance.

Description of the Related Art

The American patent application published under number US 2013/0276794 A1 describes such an implant. It is intended to protect the middle concha during a surgical operation in the nasal cavity. Thus, the use of the implant is only necessary for the time of the surgical operation. It is therefore not adapted for holding in place for a long time, for example several months.

It may thus be desired to provide an implant for medical use which allows overcoming at least part of the above-mentioned problems and constraints.

SUMMARY OF THE INVENTION

An object of the invention is therefore an implant for medical use intended to be introduced into a cavity of a human or animal body, including at least one clip comprising two walls intended to grip therebetween a biological protuberance present in the cavity in order to attach the implant to the biological protuberance, the implant being characterized in that each wall includes a structure element having undulations so that the structure element is folded up several times on itself, allowing the wall to be folded up before the introduction of the implant, then deployed inside the cavity.

Thus, the implant according to the invention can have large walls, allowing it to be stably and durably attached to the biological protuberance, while being able to be introduced into the cavity through a narrow opening.

Optionally, the structure element is a rod.

Also optionally, the implant has an elongated shape in a longitudinal direction and further includes at least one stabilizer protruding from the walls in a direction perpendicular to the longitudinal direction.

Also optionally, the implant includes a front part including a front stabilizer, a central part including the walls and a rear part including a rear stabilizer.

Also optionally, the stabilizer includes a meshed structure designed to be flattened before the introduction of the implant, then deployed inside the cavity.

Also optionally, the meshed structure has meshes each having an area of at least 0.1 cm$^2$.

Also optionally, the implant further has an anti-inflammatory and/or antimicrobial coating.

Also optionally, at least the structure element includes a shape memory material designed to deploy above a predetermined temperature.

Also optionally, at least the structure element includes a superelastic and/or resorbable material.

Also optionally, each wall of at least one of the clip(s) has a height decreasing from a rear edge to a front edge of the wall.

Also optionally, each wall of at least one of the clip(s) has a constant height from a rear edge to a front edge of the wall.

Also optionally, the implant further includes, for each wall of at least one of the clip(s), a structural reinforcement element extending along an edge of this wall.

Also optionally, each structural reinforcement element includes a rod having undulations allowing a compression of this structural reinforcement element.

Also optionally, the clip(s) comprise two clips intended to grip respectively two biological protuberances present in the cavity in order to attach the implant to both biological protuberances at the same time.

Also optionally, the two clips are located one above the other so as to be able to grip respectively a middle concha and an inferior concha of a nasal cavity.

BRIEF DESCRIPTION OF THE DRAWINGS

The invention will be better understood using the following description, given only by way of example and made with reference to the appended drawings wherein.

DESCRIPTION OF THE PREFERRED EMBODIMENTS

Figure 1:
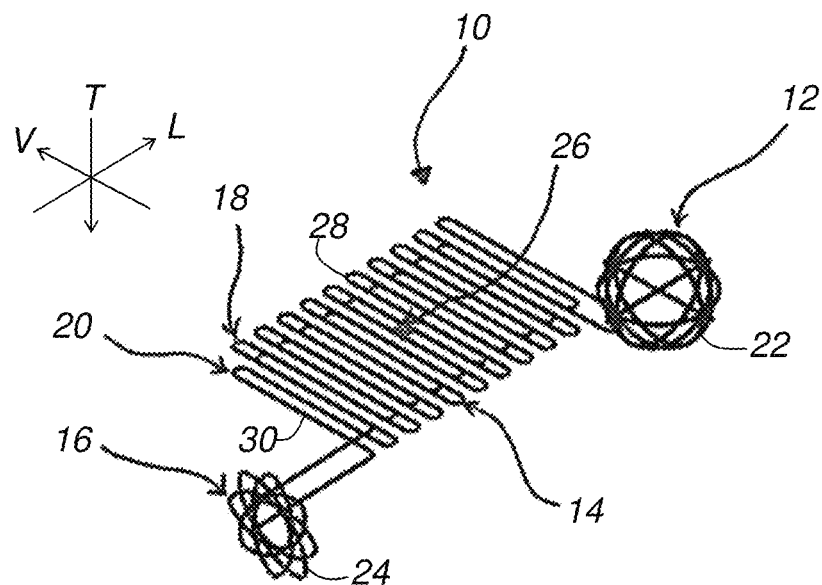
FIGS. 1 to 4 schematically show the general structure of an implant for medical use according to a first embodiment of the invention, in the deployed state, FIG. 5 schematically shows a nasal cavity of a human being, FIG. 6 schematically shows the implant in the folded-up state, FIG. 7 schematically shows a device for deploying the implant, FIG. 8 schematically shows the implant clipped on a biological protuberance, FIG. 9 schematically shows the general structure of an implant for medical use, in the deployed state, according to a second embodiment of the invention, and FIG. 10 schematically shows a compressed state of the implant of FIG. 9.

In the following description, the elements will be described with reference to an orthogonal reference frame formed of a longitudinal direction L, a vertical direction V and a transverse direction T.

The implant 10 for medical use according to a first embodiment of the invention, schematically shown in FIGS. 1 to 4 in the deployed state is of a generally elongated shape in the longitudinal direction L and has a front part 16, a central part 14 and a rear part 12.

The central part 14 is intended to clip on a biological protuberance present in a cavity of a human or animal body. For this purpose, the central part 14 includes two walls 18, 20 which extend substantially facing each other and which are intended to grip the biological protuberance therebetween. Each wall 18, 20 has a lower edge attached to the front part 16 and to the rear part 12 of the implant 10. In the described example, the two walls 18, 20 are planar and extend parallel to the plane defined by the longitudinal direction and the vertical direction. Furthermore, the walls 18, 20 have a length comprised between 30 and 50 mm, for example 40 mm, and a height comprised between 20 and 30 mm, for example 25 mm.

Moreover, in the described example, the front part 16 and the rear part 12 include respectively a front stabilizer 24 and a rear stabilizer 22 intended to stabilize the implant 10 in the cavity. For this purpose, each of the stabilizers 22, 24 protrudes vertically and/or transversely from the central part 14, so that the implant 10 has a vertical and/or transverse space requirement greater than that of the central part 14 alone, and particularly of the walls 18, 20 alone. Thus, the implant 10 is unlikely to move in the cavity, because its space requirement makes it quickly come into contact with the walls of the cavity. Furthermore, with this space requirement, the implant 10 is unlikely to pass through an opening leading to the cavity and therefore is at low risk of exiting the cavity. In the described example, the rear stabilizer 22 is disc shaped and the front stabilizer 24 is spherical shaped. Furthermore, the stabilizers 22, 24 have a diameter comprised between 10 and 20 mm, for example 15 mm. In a general manner, the shape and size of the stabilizers 22, 24 are adapted to the shape of the cavity.

The implant 10 may further include at least one sensor 26 of a biological quantity. Each sensor is for example attached on the central part 14 of the implant 10 and allows evaluating in situ at least one biological parameter such as, without being restrictive, the oxygenation level of biological tissues or else the pressure around the implant 10. Preferably, each sensor 26 includes a wireless communication system allowing to communicate the data collected by the sensor 26 towards a computing device, such as a smartphone or a tablet, located outside the human or animal body. The presence of the sensor(s) 26 on the implant 10 thus allows remotely monitoring various biological parameters, the knowledge of which is useful in otorhinolaryngology, neurosurgery or any other medical specialty.

A dedicated software can be programmed to detect a deviation of the measurements relative to a normal interval within which they should be. In case of deviation detected, an automatic alert can be sent (for example by email or by short telephone message (SMS)) to the healthcare professional so that he/she warns, for example, the patient in whom the implant 10 is placed. Alternatively or in addition, the automatic alert can be sent directly to the patient, or else to a call processing center which will be responsible for calling the healthcare professional and/or the patient. Once the measurements have been obtained, they can be used by the healthcare professional in order to react to a potentially unforeseen event once the patient has left the hospital, or to perform or refine their diagnosis, thus allowing to personalize the treatment of the patient. Moreover, the measurements obtained can be used to build up or else supply registers or any other type of database.

To facilitate the introduction of the implant 10 into the cavity, each wall 18, 20 includes a rod 28, 30 having longitudinal undulations so that the rod 28, 30 is folded up several times on itself. More specifically, the rod has vertical parallel bars linked at their ends by meanders alternating from one end to the other of the bars. Thus, each wall 18, 20 can be longitudinally folded up by bringing the bars closer to one another. Moreover, the rod 28, 30 has a front end attached to the front stabilizer 24 and a rear end attached to the rear stabilizer 22.

Still to facilitate the introduction of the implant 10, the stabilizers 22, 24 include a meshed structure designed to be flattened before the introduction of the implant 10. Preferably, the meshed structure includes meshes each having an area of at least 0.1 cm$^2$ in order to allow the flow of biological fluids through the stabilizers 22, 24.

Preferably, the rods of the walls 18, 20 and the meshed structures of the stabilizers 22, 24 are formed from a material having shape memory and/or superelasticity properties.

The shape memory property allows the material that has been deformed to return, when heated above a predetermined temperature, to the original shape thereof. For example, the material is adapted to automatically return to the deployed shape thereof when its temperature exceeds a predetermined threshold, this threshold preferably being comprised between 36° C. and 38° C., for example 37° C. These temperatures correspond to the usual temperatures in the cavities of a human or animal body.

The elasticity property allows the material having been deformed by a stress to return, when the stress stops, to the initial shape thereof (this is called elastic deformation). The superelasticity property is identical but extends to very large deformations.

Preferably, a material called "shape memory alloy" is used, because the shape memory materials have both shape memory and superelasticity properties. For example, the shape memory material used is Nitinol, a nickel-titanium alloy increasingly used in the medical field, due to its superelastic capacities, its shape memory and its good tolerance by the organism.

Furthermore, preferably, the rods 28, 30 of the walls 18, 20 and the meshes of the stabilizers 22, 24 are made from a single wire, which is folded to obtain the desired shapes, preferably without welding.

Figure 2:
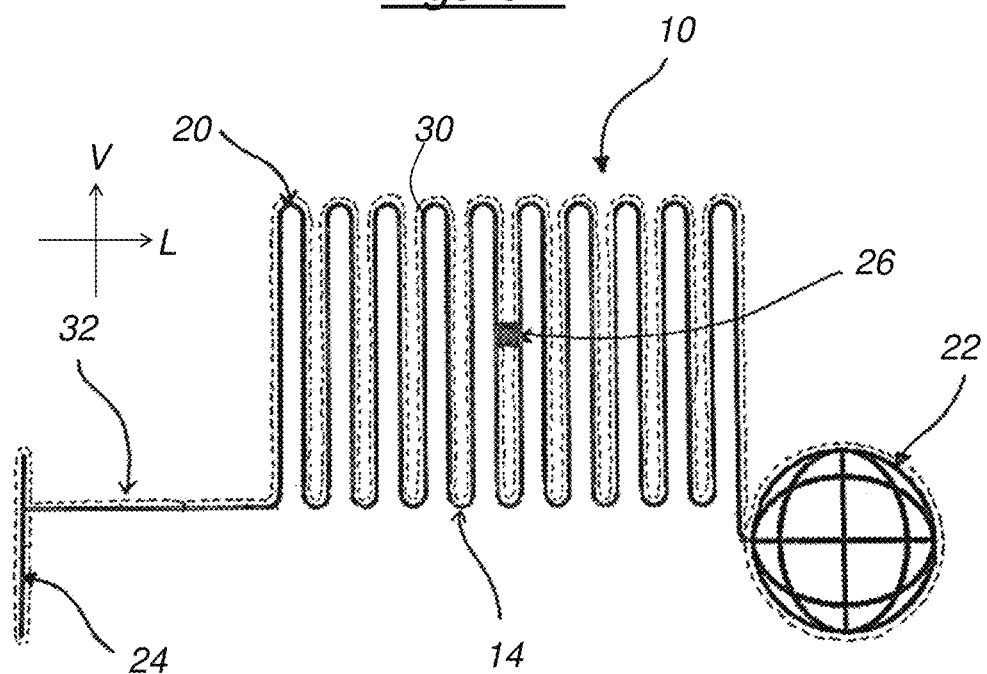
Figure 3:
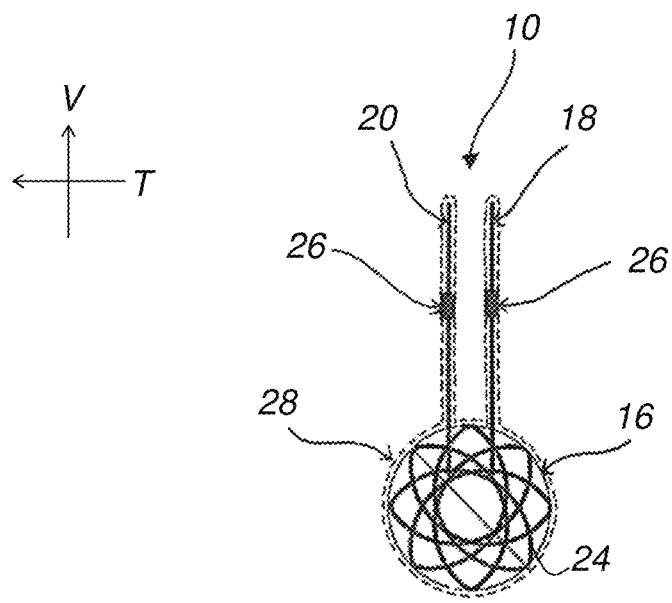
Figure 4:
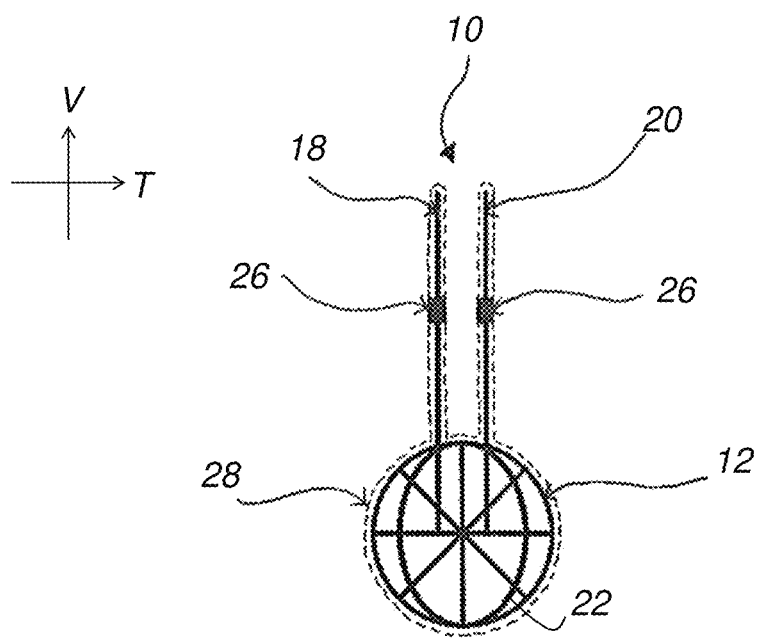

Referring to FIGS. 2 to 4, the implant 10 preferably has an anti-inflammatory and/or antimicrobial coating (shown in the figures by the dotted lines 32). Furthermore, it may have a therapeutic coating, for example anti-infectious, anti-cancer, anti-granuloma, corticosteroid coating or a coating for treating polyposis or chronic sinusitis. Each coating is capable of providing the associated treatment for a predetermined period, for example at least one week.

Figure 5:
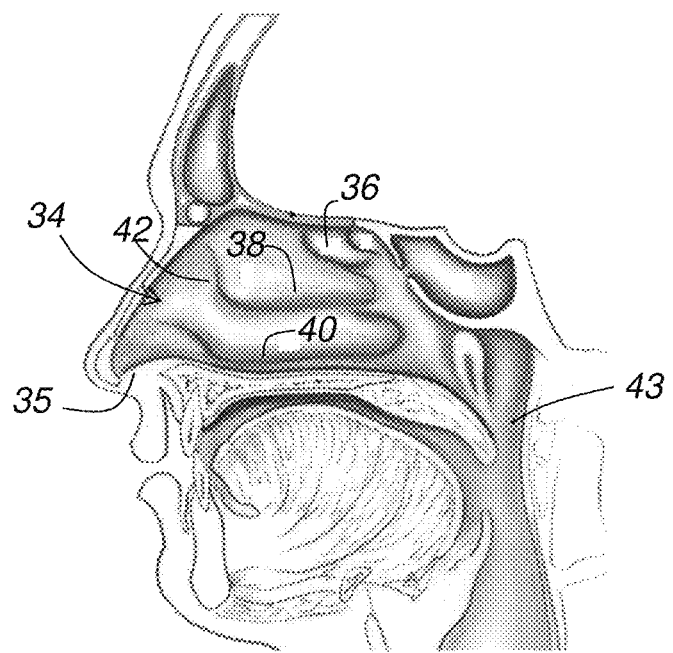

In the described example, the implant 10 is intended to be introduced into a nasal cavity 34 shown in FIG. 5. The nasal cavity 34 (also called nasal fossa) extends behind the nostril 35. The superior 36, middle 38 and inferior 40 conchas act as a filter and allow good circulation of air and other fluids. The uncinate process 42, located laterally relative to the middle concha 38 delimits the entrance of the ostium of the maxillary sinus.

After a surgery affecting the middle concha 38 and/or the uncinate process 42, the integrity of the mucosa of the nasal cavity 34 may be affected. Therefore, there is a risk that the middle concha 38 will lateralize, that is to say that it will adhere to the uncinate process and/or to the inferior concha 40 and cause an unwanted scarring. In the described example, the implant 10 aims at reducing the risk of lateralization of the middle concha 38.

Figure 6:
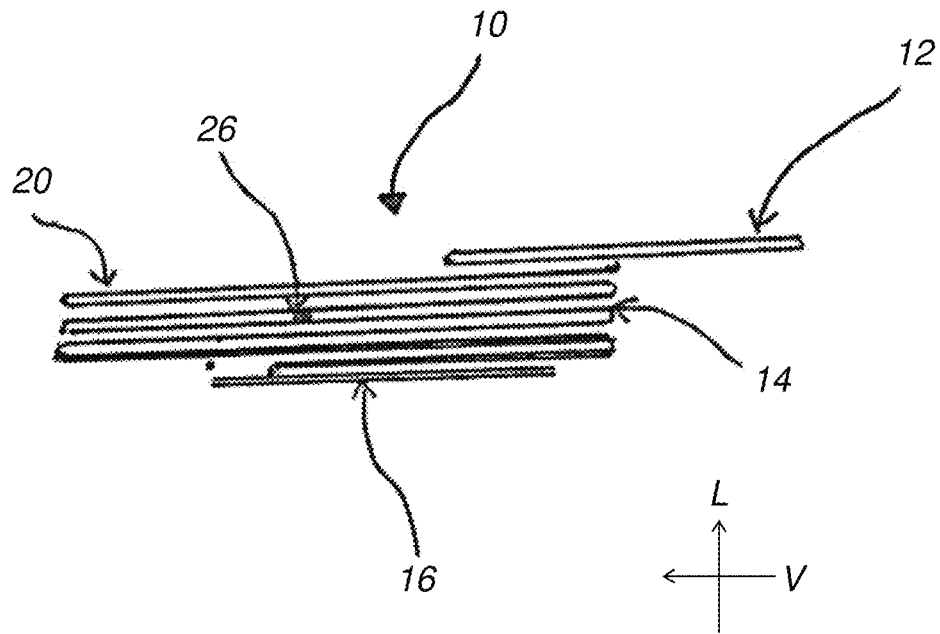

With reference to FIG. 6, the implant 10 is illustrated in a folded-up state wherein the walls 18, 20 are folded up along the longitudinal direction L and the stabilizers 22, 24 are flattened and straightened in the plane defined by the vertical direction V and the transverse direction T. Thus, the implant 10 is very compact and has an elongated shape along the vertical direction V.

Figure 7:
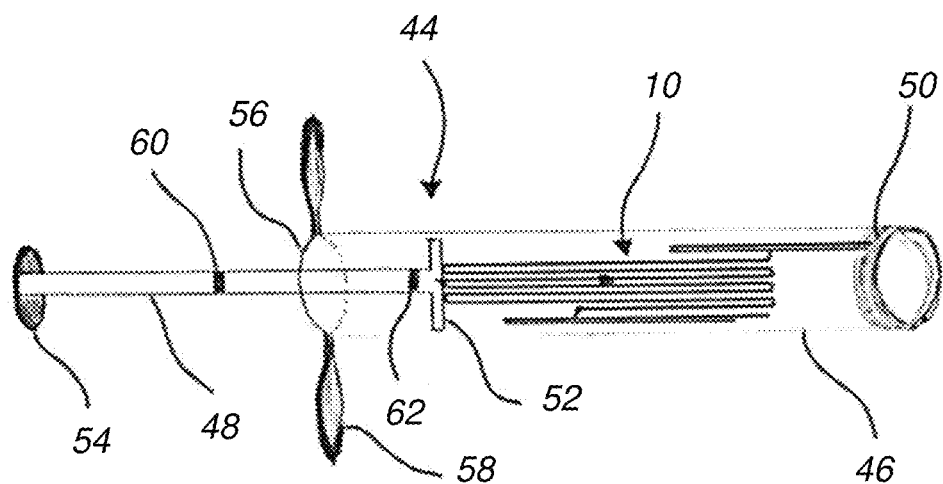

A deployment device 44 illustrated in FIG. 7 can be used to deploy the implant 10 in the nasal cavity 34.

The deployment device 44 has the general shape of a syringe with a hollow tube 46, which is preferably transparent, wherein the implant 10 in the folded-up state is intended to be placed and a piston 48 sliding in the hollow tube 46 to push the implant 10 to a distal end 50 of the hollow tube 46. Preferably, the distal end 50 is made of a more flexible material than the rest of the hollow tube 46 so as not to damage the mucosa during its introduction and thus increase the comfort of the patient.

The piston 48 is rigid and has, at a distal end, a plate 52 and, at a proximal end, a push button 54. The deployment device 44 further includes, at a proximal end 56 of the hollow tube 46, retraction fins 58 allowing, in cooperation with the push button 54, a user to manually slide the piston 48 relative to the hollow tube 46.

The piston 48 is provided with a medial marker 60 and a distal marker 62. The distal marker 62 is separated from the push button 54 by a distance corresponding to the length (along the vertical direction V) of the implant 10 in the folded-up state. The markers 60, 62 are intended to ensure the correct positioning of the implant 10 in the nasal cavity 34, as will be explained thereafter.

To introduce the implant 10 into the nasal cavity 34, the hollow tube 46 containing the implant 10 is inserted into the nostril 35 then into the nasal cavity 34 until bringing its proximal end 56 at the entrance of the nostril 35. The piston 48 is then inserted into the hollow tube 46 through its proximal end 56, the plate 52 coming into contact with the implant 10. By simultaneous action on the push button 54 and the retraction fins 58, the hollow tube 46 is then gradually extracted from the nasal cavity 34 while the piston 48 expels the implant 10 into the nasal cavity 34 through the distal end 50 of the hollow tube 46, in the proximity of the middle concha 38.

The markers 60, 62 allow location during this phase. More specifically, the alignment of the distal marker 62 with the proximal end 56 of the hollow tube 46 indicates that the implant 10 is about to begin to exit the distal end 50 of the hollow tube 46. Furthermore, the alignment of the medial marker 60 with the proximal end 56 of the hollow tube 46 indicates that half of the implant 10 has exited the hollow tube 46 through its distal end 50. Finally, the contact between the push button 54 and the proximal end 56 of the hollow tube 46 indicates that all of the implant 10 has exited the hollow tube 46.

Figure 8:
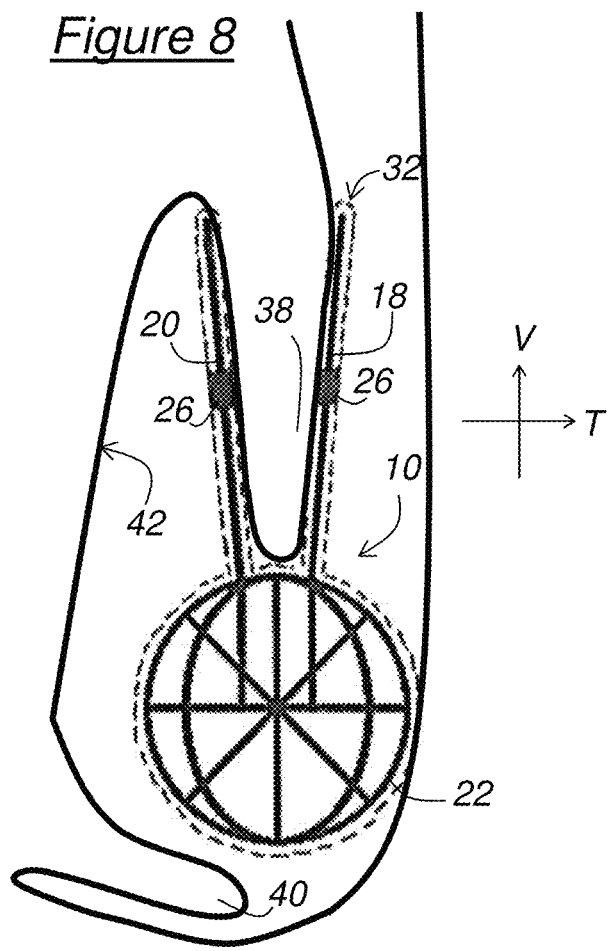

The temperature in the nasal cavity 34 being approximately 37° C., the shape memory implant 10 is heated by the nasal cavity 34 to 37° C., which is above the deployment threshold so that the implant 10 deploys, that is to say it automatically returns to the configuration illustrated in FIGS. 1 to 4. Alternatively, when the superelasticity property is used, the implant 10 automatically returns to the initial shape thereof when it exits the hollow tube 46, since the stress exerted by the latter on the implant 10 stops. In either case, the two walls 18, 20 deploy on either side of the middle concha 38 so as to grip it as illustrated in FIG. 8. Thus, the implant 10 is clipped on the middle concha 38 and firmly secured in the nasal cavity 34. Furthermore, the presence of stabilizers 22, 24 prevents its expulsion through the nostril 35, or else its ingestion by the oropharynx 43, as illustrated in FIG. 5. In this position, the implant 10 forms a physical barrier to prevent the middle concha 38 from coming into contact with the uncinate process 42 and/or the inferior concha 40. Furthermore, the anti-inflammatory and/or antimicrobial coating 32 allows rapid scarring of raw tissue and therefore reduces the risk of lateralization of the middle concha 38. Moreover, the coating 32 can also allow, without surgical intervention necessarily having been performed, treating polyposis, sinusitis or any other illness of the nasal fossa that the coating 32 is adapted to treat. Finally, the mesh of stabilizers 22, 24 allows the nasal cavity 34 to be washed.

Figure 9:
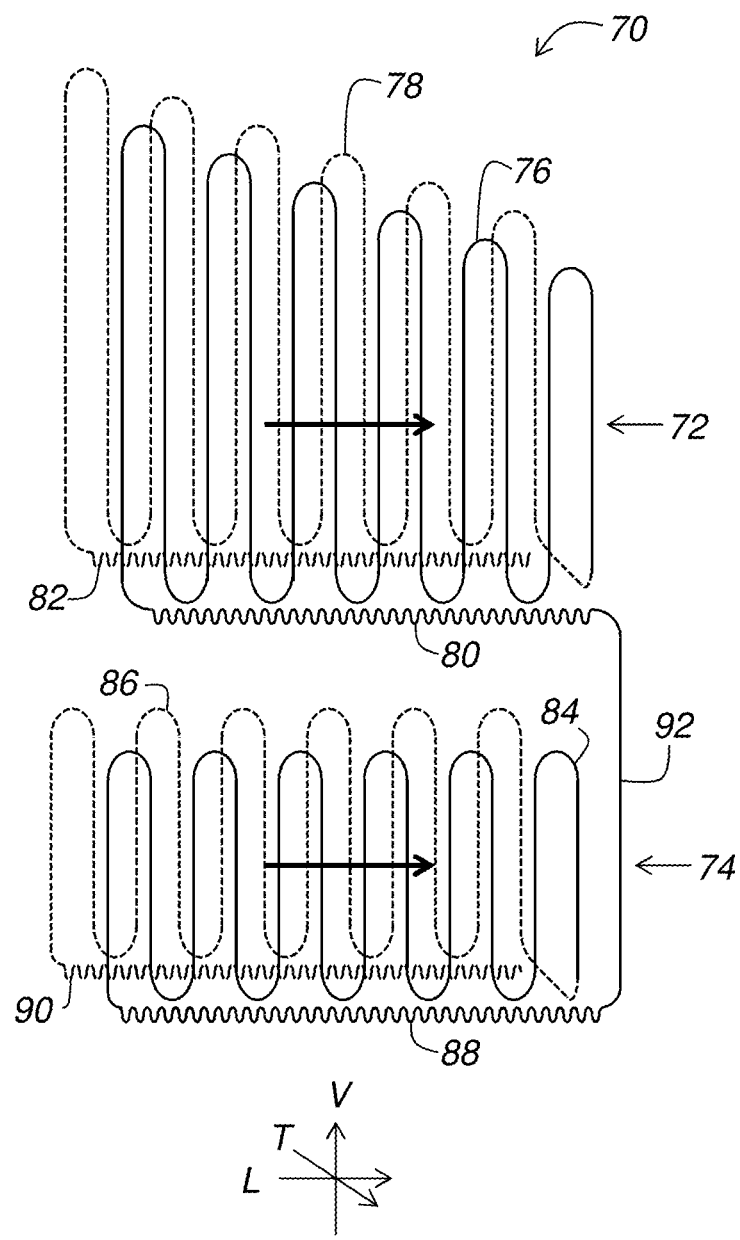

An implant 70 for medical use according to a second embodiment of the invention, is schematically shown in the deployed state in FIG. 9. The implant 70 includes two parts 72, 74 intended to clip respectively to two biological protuberances present in a cavity of a human or animal body. In the example described, the two parts 72, 74 are vertically superimposed on each other. For example, the upper part 72 is intended to clip to the middle concha 38, while the lower part 74 is intended to clip to the inferior concha 40.

For this purpose, each part 72, 74 is made in a similar manner to the central part 14 of the implant 10 according to the first embodiment of the invention.

Thus, the upper part 72 includes two walls, respectively defined by two rods 76, 78 having longitudinal undulations, which extend substantially facing each other and which are intended to grip the first biological protuberance therebetween. The wall located in the background in FIG. 9 is shown in dotted lines to distinguish it from the wall in the foreground. In the described example, the two walls are planar and extend parallel to the plane defined by the longitudinal direction L and the vertical direction V. For example, the walls have a length comprised between 30 and 50 mm, for example 40 mm, and a height comprised between 20 and 30 mm, for example 25 mm. Due to the longitudinal undulations, each rod 76, 78 is folded up several times on itself. More specifically, each rod 76, 78 has vertical parallel bars linked at their ends by meanders alternating from one end to the other of the bars. Thus, each wall can be longitudinally folded up by bringing the bars closer to one another. In the described example, these bars have lengths which decrease from the rear to the front, so that each wall has a height decreasing from a rear edge to a front edge of the wall.

The upper part 72 further includes, for each wall, a structural reinforcement element extending longitudinally along a lower edge of the wall. In the described example, each structural reinforcement element includes a respective rod 80, 82 having longitudinal undulations in order to allow the longitudinal compression of the structural reinforcement element at the same time as that of the associated wall. The longitudinal undulations of the rods 80, 82 have a height much smaller than the undulations of the rods 76, 78, for example at least ten times smaller.

Similarly, the lower part 74 includes two walls defined respectively by two rods 84, 86 having longitudinal undulations. In the described example, the walls of the lower part 74 have a constant height, for example comprised between 10 and 30 mm. The lower part 74 further includes two structural reinforcement elements extending longitudinally along the lower edges respectively of the walls. These structural reinforcement elements include in the described example respectively two rods 88, 90 having longitudinal undulations, as for the upper part 72, these longitudinal undulations having a height much smaller than that of the longitudinal undulations of the rods 86, 84, for example at least ten times smaller.

The implant 70 further includes a linking element attaching the lower part 74 to the upper part 72. In the described example, this linking element includes a substantially vertical rod 92 connecting the front ends of two structural reinforcement elements respectively of the upper 72 and lower 74 parts.

As for the implant 10 according to the first embodiment, the rods 76-92 are for example made of a material having shape memory and/or superelasticity properties.

Furthermore, preferably, the rods 76-92 are made from a single wire, folded up to obtain the desired shapes, preferably without welding.

Furthermore, preferably, the rods 76-92 are made of a resorbable material, that is to say that the material is adapted to completely disappear by progressive absorption under the effect of the biological environment of the cavity, for example in less than two years. Preferably, when a resorbable material is used, no welding is provided.

It will further be appreciated that, in the described example, the implant 70 is devoid of a sensor.

Figure 10:
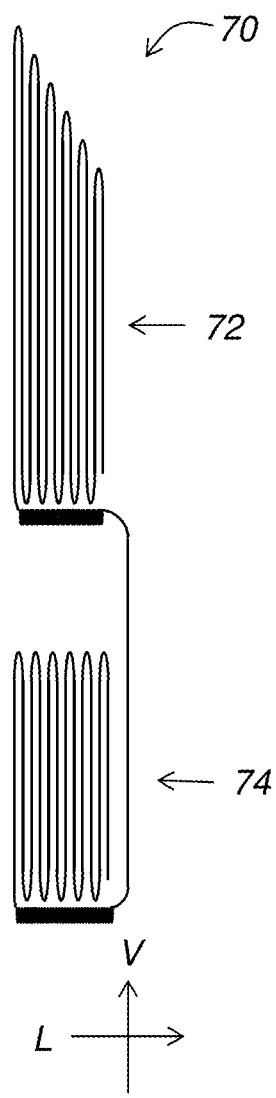

Thus, the walls defined by the rods 76, 78, 84, 86, as well as the structural reinforcement elements formed by the rods 80, 82, 88, 90, can be longitudinally folded up on themselves, as indicated by the two bold arrows in FIG. 9, to obtain the compressed state illustrated in FIG. 10. In this compressed state, the implant 70 can be introduced into the nasal cavity 34 to be deployed therein reverting to the deployed state of FIG. 9, with the clip formed by the upper part 72 gripping the middle concha 38 and the clip formed by the lower part 74 gripping the inferior concha 40.

It clearly appears that an implant for medical use such as those described above is capable of clipping in a sustainable manner on a biological protuberance, while being able to be easily introduced in the folded-up state into the cavity. It is particularly adapted for otorhinolaryngology surgery procedures, or even in neurosurgery, or in any other type of surgical specialty requiring the use of this type of implant. In this case, the shapes of the implant 10 or 70 can be adapted to all the desired applications, and can therefore be very diverse.

Moreover, it will be noted that the invention is not limited to the embodiments described above. Indeed, it will appear to the person skilled in the art that various modifications can be made to the embodiment described above, in light of the teaching which has just been disclosed to them.

Particularly, each wall could include, instead of the rod, an accordion-folded sheet.

In the following claims, the terms used should not be interpreted as limiting the claims to the embodiments described in the present description, but should be interpreted to include all the equivalents that the claims aim at covering due to their formulation and whose prediction is within the reach of the person skilled in the art by applying their general knowledge to the implementation of the teaching which has just been disclosed.

The invention claimed is:

1. An implant (10; 70) for medical use intended to be introduced into a cavity (34) of a human or animal body, the implant comprising:
   at least one clip comprising two parallel planar walls (18, 20),
   wherein respective planes of the two parallel planar walls extend substantially facing each other so that the two parallel planar walls are configured to grip therebetween a biological protuberance (38) present in the cavity (34) in order to attach the implant (10) to the biological protuberance (38),
   wherein each of the two parallel planar walls (18, 20) includes a structure element (28, 30; 76, 78; 84, 86) having longitudinal undulations so that the structure element (28, 30; 76, 78; 84, 86) is folded up more than one time on itself, allowing each of the two parallel planar walls (18, 20) to be folded up before the introduction of the implant (10; 70), then deployed inside the cavity (34).

2. The implant (10; 70) according to claim 1, wherein the structure element (28, 30; 76, 78; 84, 86) is a rod comprised of parallel bars having ends linked by meanders alternating from one end to another end of the parallel bars such that each of the two parallel walls is configured to be folded up more than one time on itself by bringing the parallel bars closer to one another.

3. The implant (10) according to claim 2, having an elongated shape in a longitudinal direction (L) and further including at least one stabilizer (22, 24) protruding from each of the two parallel planar walls (18, 20) in a direction perpendicular (V, T) to the longitudinal direction (L).

4. The implant (10; 70) according to claim 2, further having an anti-inflammatory and/or antimicrobial coating (32).

5. The implant (10) according to claim 1, further comprising an elongated shape in a longitudinal direction (L) and further including at least one stabilizer (22, 24) protruding from each of the two parallel planar walls (18, 20) in a direction perpendicular (V, T) to the longitudinal direction (L).

6. The implant (10) according to claim 5, further comprising a front part (16) including a front stabilizer (24), a central part (14) including the two parallel planar walls (18, 20) and a rear part (12) including a rear stabilizer (22).

7. The implant (10) according to claim 6, wherein the at least one stabilizer (22, 24) includes a meshed structure designed to be flattened before the introduction of the implant (10), then deployed inside the cavity (34).

8. The implant (10; 70) according to claim 6, further having an anti-inflammatory and/or antimicrobial coating (32).

9. The implant (10) according to claim 5, wherein the at least one stabilizer (22, 24) includes a meshed structure designed to be flattened before the introduction of the implant (10), then deployed inside the cavity (34).

10. The implant (10) according to claim 9, wherein the meshed structure has meshes each having an area of at least 0.1 cm2.

11. The implant (10; 70) according to claim 5, further having an anti-inflammatory and/or antimicrobial coating (32).

12. The implant (10; 70) according to claim 1, further comprising an anti-inflammatory and/or antimicrobial coating (32).

13. The implant (10; 70) according to claim 1, wherein at least the structure element (28, 30; 76, 78; 84, 86) includes a shape memory material designed to deploy above a predetermined temperature.

14. The implant (10; 70) according to claim 1, wherein the structure element (28, 30; 76, 78; 84, 86) includes a super-elastic and/or resorbable material.

15. The implant (70) according to claim 1, wherein each of the two parallel planar walls of at least one of the clip(s) has a height decreasing from a rear edge to a front edge of the planar wall.

16. The implant (10; 70) according to claim 1, wherein each of the two parallel planar walls of at least one of the clip(s) has a constant height from a rear edge to a front edge of the planar wall.

17. The implant (70) according to claim 1, further including, for each of the two parallel planar walls of at least one of the clip(s), a structural reinforcement element extending along an edge of this planar wall.

18. The implant (70) according to claim 17, wherein each structural reinforcement element includes a rod (80, 82, 88,

90) having undulations allowing a compression of this structural reinforcement element.

19. The implant (70) according to claim 1, wherein the at least one clip comprises two clips intended to grip respectively two biological protuberances (38, 40) present in the cavity (34) in order to attach the implant (70) to both biological protuberances at the same time.

20. The implant (70) according to claim 19, wherein the two clips are located one above the other so as to be able to grip respectively a middle concha (38) and an inferior concha (40) of a nasal cavity (34).

\* \* \* \* \*